United States Patent [19]
Grim et al.

[11] Patent Number: 5,695,452
[45] Date of Patent: *Dec. 9, 1997

[54] FORMED RESILIENT ORTHOPAEDIC DEVICE

[76] Inventors: Tracy E. Grim, 3010 W. Boston Ct., Broken Arrow, Okla. 74012; Kevin R. O'Donnell, 282 W. Sidlee St., Thousand Oaks, Calif. 91360; Alec D. Bobroff, 12865 Glen Brae Dr., Saratoga, Calif. 95070; Mark D. Holt, 12570 Sunnyglen St., Moorpark, Calif. 93021; Joseph M. Iglesias, 5300 Oak Park La., #104, Agoura, Calif. 93101; John M. Bourne, 1323 S. Gertruda Ave., Redondo Beach, Calif. 90277; William K. Arnold, 2330 E. Delmar, Pasadena, Calif. 91107

[*] Notice: The term of this patent shall not extend beyond the expiration date of Pat. No. 5,334,135.

[21] Appl. No.: 252,600

[22] Filed: Jun. 1, 1994

Related U.S. Application Data

[63] Continuation-in-part of Ser. No. 18,004, Feb. 16, 1993, Pat. No. 5,334,135.

[51] Int. Cl.⁶ ........................................... A61F 5/00
[52] U.S. Cl. .................... 602/6; 602/7; 602/26; 602/27; 602/19
[58] Field of Search ................ 602/5–8, 14, 23, 602/27–29, 18–20, 26, 41, 46, 60–63

[56] References Cited

U.S. PATENT DOCUMENTS

| | | |
|---|---|---|
| 3,587,572 | 6/1971 | Evans . |
| 3,692,023 | 9/1972 | Phillips et al. .................. 602/7 |
| 3,930,496 | 1/1976 | Gibbons . |
| 3,942,522 | 3/1976 | Wilson . |
| 4,066,074 | 1/1978 | Keller . |
| 4,454,871 | 6/1984 | Mann et al. .................. 602/27 |
| 4,632,106 | 12/1986 | Gamm . |
| 4,685,453 | 8/1987 | Guignard et al. . |
| 4,738,257 | 4/1988 | Meyer et al. .................. 602/48 |
| 4,821,708 | 4/1989 | Guignard et al. . |
| 4,888,225 | 12/1989 | Sandvig et al. .................. 602/8 X |
| 4,928,678 | 5/1990 | Grim . |
| 4,940,043 | 7/1990 | Burns et al. .................. 602/18 |
| 4,953,543 | 9/1990 | Grim et al. . |
| 4,964,402 | 10/1990 | Grim et al. .................. 602/27 X |
| 4,993,409 | 2/1991 | Grim . |
| 5,002,047 | 3/1991 | Sandvig et al. .................. 602/8 |
| 5,027,801 | 7/1991 | Grim . |
| 5,030,402 | 7/1991 | Zachariades .................. 204/138 |
| 5,031,607 | 7/1991 | Peters .................. 602/27 |
| 5,062,414 | 11/1991 | Grim . |
| 5,088,478 | 2/1992 | Grim . |
| 5,195,945 | 3/1993 | Sandvig et al. .................. 602/8 |
| 5,324,252 | 6/1994 | Libbey et al. .................. 602/5 |
| 5,334,135 | 8/1994 | Grim et al. .................. 602/26 |

*Primary Examiner*—Linda C. Dvorak
*Attorney, Agent, or Firm*—Oppenheimer Poms Smith

[57] ABSTRACT

An orthopaedic support includes a sheet of foam material that has been compression molded in specific areas. These areas have a thickness and density that is different from other areas of the support and serve to better fit the support to the body. The support may include compression molded grooves or cavities to accommodate straps, struts, gel-filled pads, inflatable bladders, pumps, and other accessories. The support may also include compression molded grooves that reduce bunching when the support is bent, and may include molded edges to minimize skin irritation during activity. The brace may also be a back brace or an ankle brace having compression molded components. A method of compression molding an orthopaedic support includes compression molding at least one sheet of resilient foam material in selected areas to reduce the thickness and increase the density of the material in those areas. Various embodiments of the present invention may include compression-molded bladders having walls which are compression-molded about the bladder perimeter.

35 Claims, 8 Drawing Sheets

FIG. 10
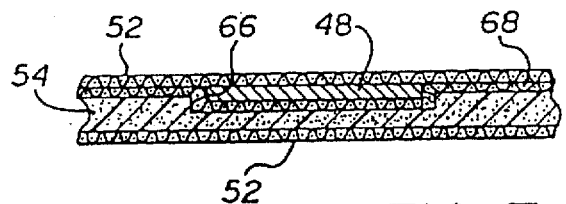
FIG. 7
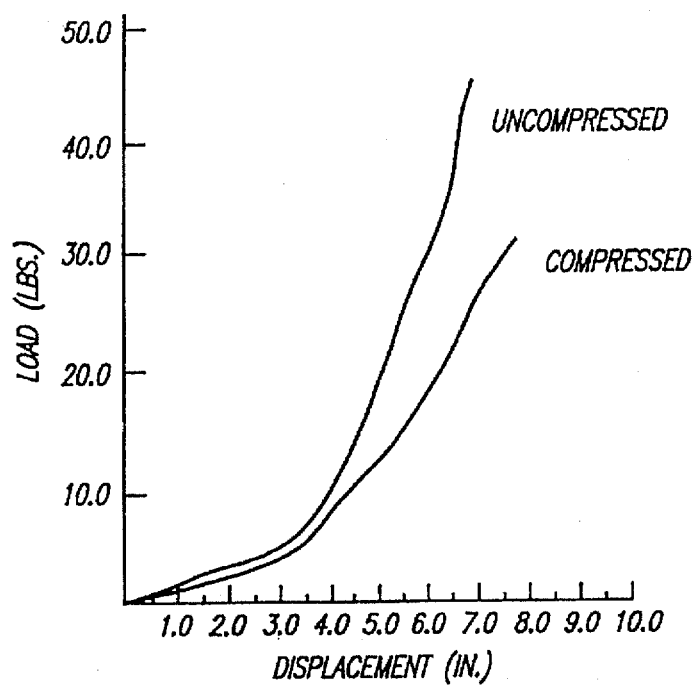
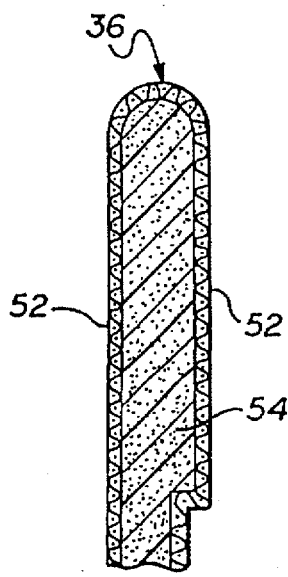
FIG. 8
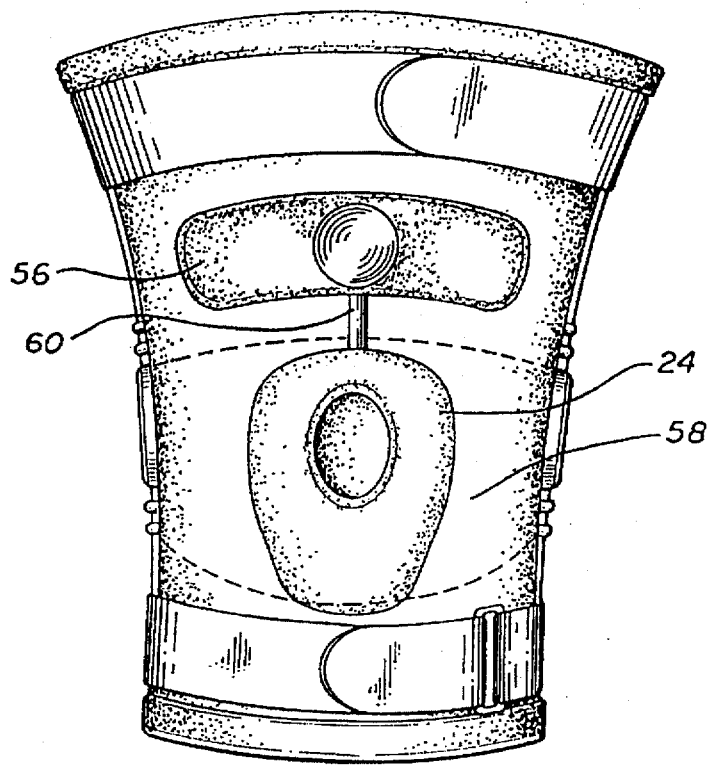
FIG. 9

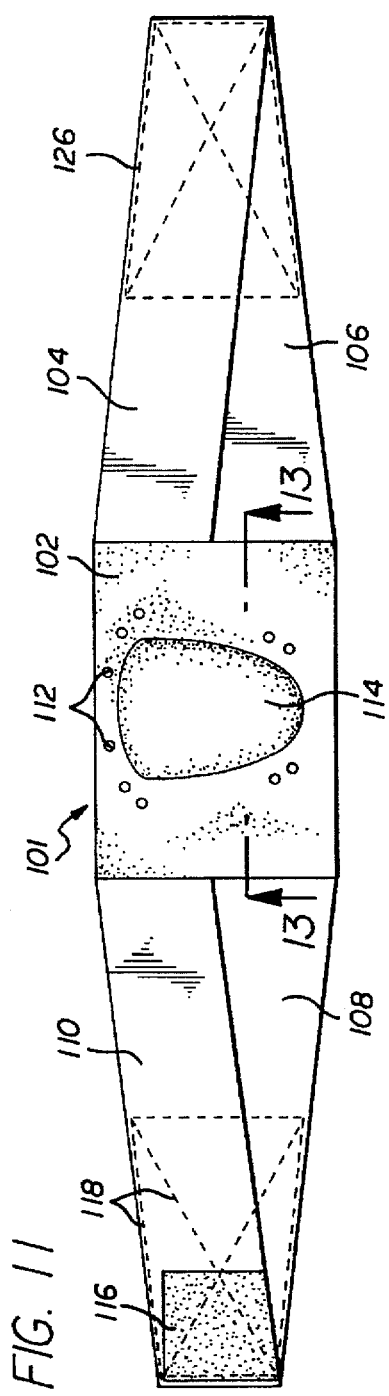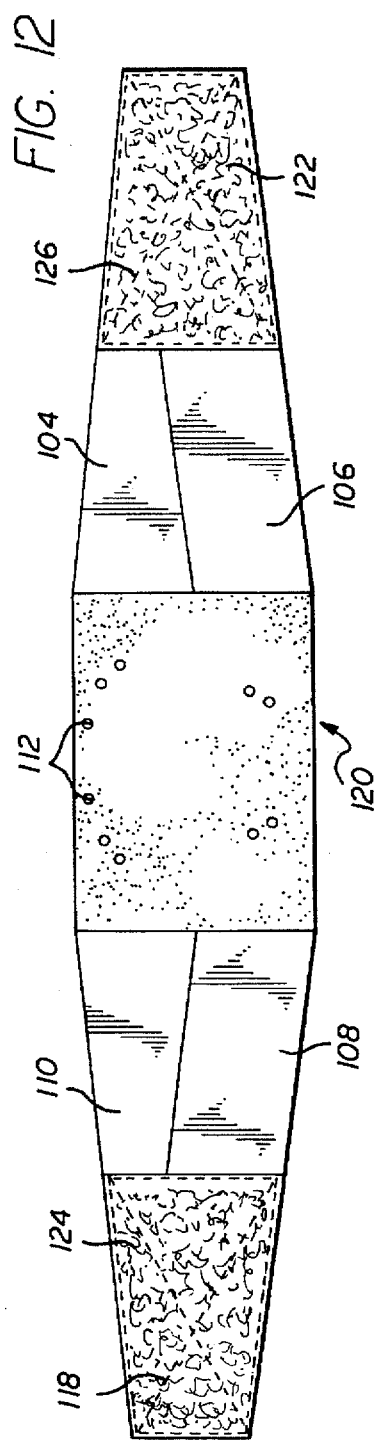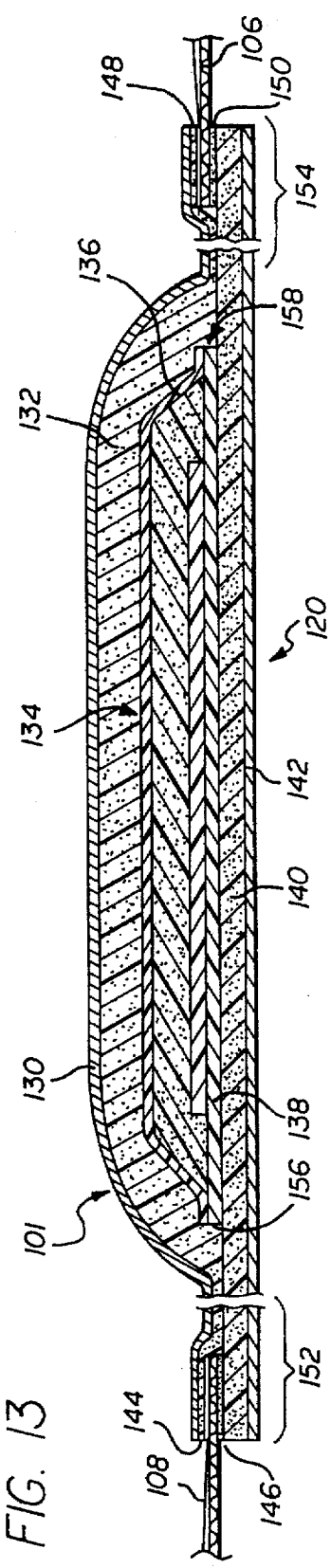

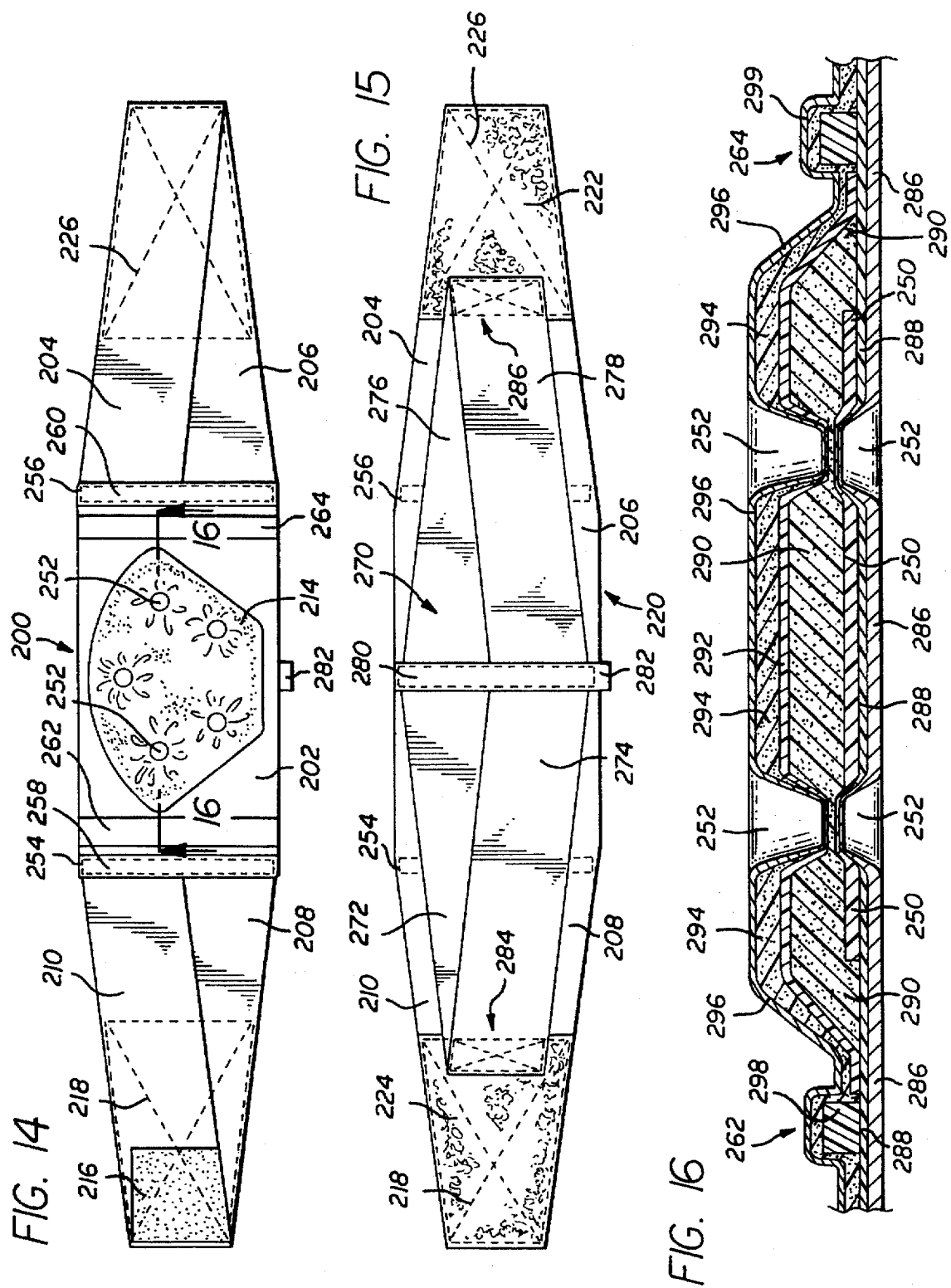

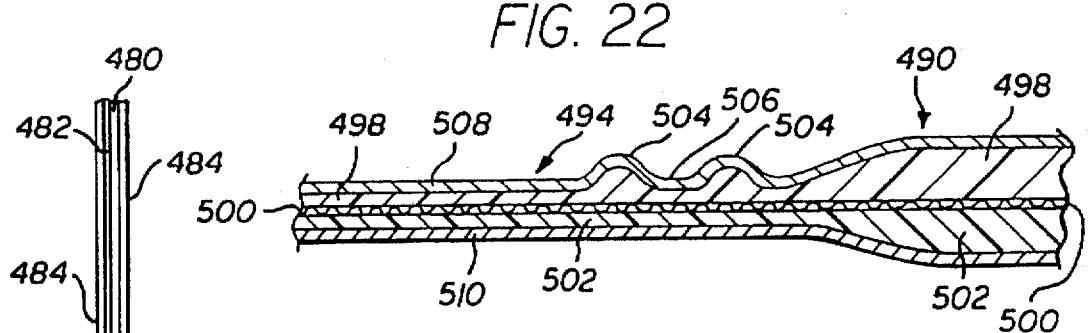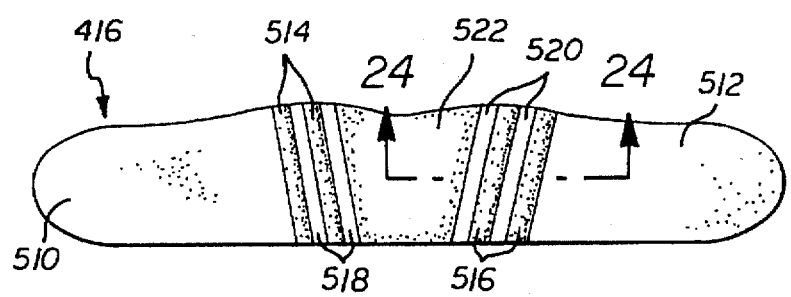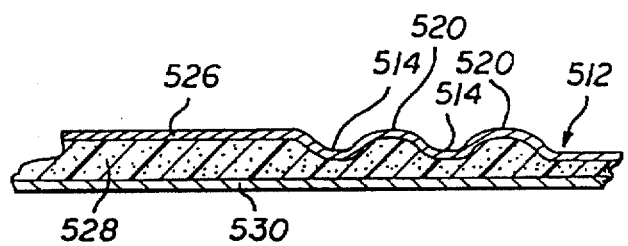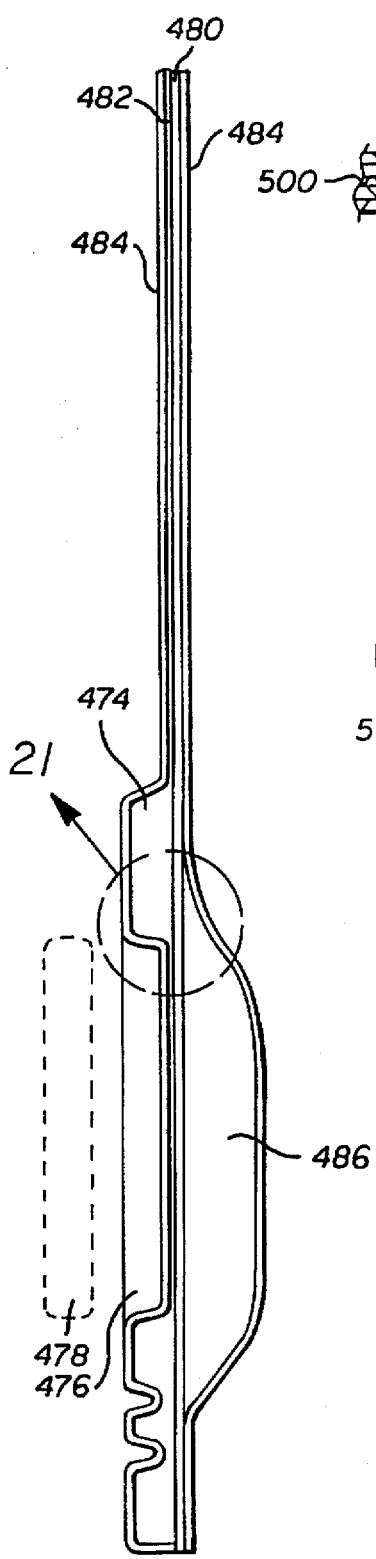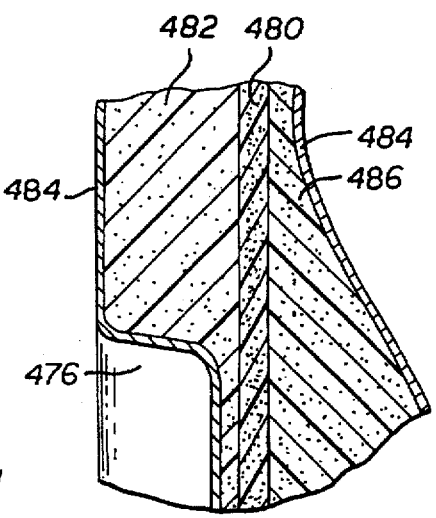

FORMED RESILIENT ORTHOPAEDIC DEVICE

RELATED APPLICATIONS

This is a continuation-in-part of U.S. patent application Ser. No. 08/018,004, filed on Feb. 16, 1993, now U.S. Pat. No. 5,334,135.

FIELD OF THE INVENTION

The present invention generally relates to orthopaedic devices for the human anatomy and, more particularly, to an orthopaedic device that is compression molded to improve the fit and performance of the support.

BACKGROUND OF THE INVENTION

Orthopaedic supports are typically used to stabilize and protect certain injured parts of the human anatomy. Such supports have often been used on knees, elbows, ankles, wrists, thighs and backs. These supports are intended to reduce strain on the injured body part, thereby allowing the injury to heal. Some supports have included struts and other hardware to help relieve some of the load from the injured part, and to restrict motion.

One such orthopaedic support is constructed as follows. First, the manufacturer cuts a base layer from a sheet of material, such as foam rubber. The manufacturer then sews a variety of pads onto the base layer, which may include buttresses, condylar pads, and popliteal pads. The manufacturer then sews on straps, which are used to secure the support to a limb. The manufacturer may also attach hardware to the support, or may sandwich such hardware between the base layer of material and a pad.

A number of problems arise with this common type of support. The first problem relates to the manufacturing process. To construct such a support, the manufacturer must cut the pads from a piece of material, position those pads onto the base layer, and sew the pads into place. The process of cutting, sewing, and positioning is labor-intensive and can become expensive. If a pad is improperly positioned and sewn, the entire support may need to be discarded as defective. Furthermore, material is wasted when the cutting process produces scrap pieces that must be thrown away.

A second set of problems arises with the support characteristics of this common type of orthopaedic support. First, the typical support stretches in order to roughly conform to the shape of joints and limbs. However, mere stretching cannot allow the support to closely conform to the nuances in the shape of the limb or joint, particularly in the case of knees, elbows and ankles. As a result, areas of the limb or joint are left under-supported or even entirely unsupported.

Another problem arises because the typical support has a base that is of uniform thickness and density, thereby producing uniform circumferential compression. Such compression cannot be increased or decreased to provide more or less support in selected areas of the injured limb or joint, in the absence of supplemental material straps. Consequently, such a support tends to shift position on the limb because there are no regions of high pressure to anchor it. Furthermore, a support having uniform thickness and density may allow the limb to move with equal ease in a variety of directions. Such ease of movement may increase the likelihood that a particular injury such as a patella injury will be aggravated.

A third set of problems arises with respect to the performance of the typical support. One problem is that the support material tends to bunch up whenever the limb is flexed. This bunching tends to interfere with the motion of the limb, is uncomfortable to the user, and may rub or chafe the skin and even bruise the skin. Another problem is that the edges of the typical support are die-cut, thereby exposing the user's skin to potentially allergenic support materials, such as neoprene. The edges tend to be rather rough, causing skin irritation during exercise.

An additional set of problems stems from hardware that may be attached to the typical support. Such hardware may include gel packs, inflatable bladders, pumps, straps, and struts. This hardware tends to protrude from the base of the support and can get caught on other objects. Since the hardware is typically sewn onto the base, the stitches can be ripped from the base and the hardware torn free. A special problem arises with hinged strut mechanisms, which can be twisted out of place so that the hinged strut does not properly guide and support the flexing motion of the joint.

SUMMARY OF THE INVENTION

There are a number of objects of the present invention. One object is to provide an orthopaedic support having varied thickness and material density. This support may be manufactured without having to cut and sew extra padding pieces. The varied thickness allows the manufacturer to increase or decrease the pressure provided to selected areas of the limb, including pressure that will prevent the support from shifting position. The varied density may allow the manufacturer to limit the range of limb motion in certain directions, in embodiments directed to use on a limb.

Another object of the present invention is to provide an orthopaedic support molded to generally conform to the contour of the part of the human anatomy that it supports. The edges may be shaped so that the skin is not exposed to allergenic or rough-edged material. The support should also not bunch up when a limb is flexed.

An additional object of the present invention is to provide an orthopaedic support having grooves to accommodate hardware. These grooves allow the hardware to remain close to the base of the support, maintain the proper position of the hardware, and act as hardware locators for ease of support assembly. Moreover, the grooves particularly act as locators for removable materials, and as gel pads, straps, etc., ensuring proper placement when re-attached.

Generally stated, an orthopaedic support that satisfies the foregoing objects includes a sheet of foam material, preferably foam rubber, that has been compression molded in specific areas. These areas have a thickness and density that is different from other areas of the support and which serve to better fit the support to the body. Such supports can be manufactured for use on various parts of the human anatomy.

Embodiments of the invention may include a number of features. The support may include compression molded grooves or cavities to accommodate straps, struts, gel-filled pads, inflatable bladders, pumps, and other accessories. The support may be compression molded into a shape that conforms to the general contour of the part of the human anatomy that it supports. The support may also include a number of compression molded grooves that reduce bunching when the support is bent. Edges of the support may have molded radii for minimizing skin irritation during activity.

One specific embodiment of the invention is a knee brace, which is manufactured from a sheet of foam rubber. The knee brace includes a front side to accommodate the patella and a rear popliteal side. Compression molded grooves extend across the popliteal side to reduce material bunching when the user bends her or his knee. The knee brace may also have a variety of compression molded pads and buttresses, as well as hardware and compression molded grooves and cavities to support that hardware.

As is apparent from the foregoing description, the present orthopaedic support readily satisfies the objects of the invention. The compression molded support is manufactured without having to cut and sew extra padding pieces. The variable thickness and density provide pressure to selected areas of a limb and improve the range of motion in certain directions. The shape of the support conforms to the contour of the part of the human anatomy that it supports, and the molded edges protect the user's skin from allergic reactions and abrasion. The compression molded grooves serve to prevent bunching of the material when the limb is flexed. Furthermore, other compression molded grooves accommodate hardware, act to maintain the hardware in proper position, and serve as hardware locators during assembly of the support.

The present invention also encompasses a compression molded back brace. The brace may have a central portion that includes resilient sheet material having a predetermined thickness and density. The resilient material is compression molded in specific areas to alter the thickness and/or density of the material in those areas in order to improve the function of the brace. Lateral support straps may be connected to the central portion. A fastening element or system holds the brace in a desired position about the user and maintains a proper fit.

Various additional features may be incorporated into alternative embodiments of the back brace. The central portion may be made of layers of material stacked upon each other. The central portion may have ventilation holes to ventilate the user's back. The lateral support straps may be sewn onto the central portion, or they may be adhered with a pressure sensitive adhesive. The lateral support straps may alternatively be integral with the central portion. The back brace may have grooves compression molded into the surface to improve the performance of the brace. The brace may include compression molded indentations and/or channels to accommodate brace hardware.

The central portion of the back brace may also include an optional, compression molded bladder. The walls of the bladder may be a material such as thin urethane or a closed-cell foam. The edges of the bladder are compression molded. The bladder may be completely sealed so that air cannot flow in and out of the bladder. The interior of the bladder may include a piece of open-cell foam for pre-inflating the bladder. Alternatively, an inflation duct may be connected at one end to the bladder to allow a user to adjustably inflate the bladder.

The present invention also includes a method of manufacturing compression molded orthopedic supports. The method includes stacking sheets of material in a stack. At least one of the sheets should be a resilient material. The stack is then compression molded in selected areas to alter the thickness and density of the support to improve the function of the support.

Selected sheets may be adhered together with an adhesive. The stack may include at least one layer of substantially non-stretchable material to limit the stretchability of at least a portion of the support. The method may include the step of adding at least one pad to a selected area of the stack prior to the step of compression molding the stack. A sheet of substantially rigid material may be added to the stack to create a stay within the support.

The method may also include the step of creating a compression molded, pre-inflated bladder within the back brace. A first and second sheet of air-impermeable material are added to the stack. A foam pad is situated in between the two sheets of air-impermeable material. The first and second sheets are adjacent to one another around the periphery of the foam pad. The step of creating a compression molded, pre-inflated bladder further includes compression molding the first and second sheets to fuse the sheets together around the periphery of the foam pad.

More generally, a compression molded brace for a portion of the human anatomy is constructed from at least one sheet of resilient foam material having a predetermined thickness and density. The sheet is compression molded in certain areas to reduce the thickness and increase the density of the material in the compression molded areas. Areas of less dense material which serve as padding and areas of more dense material which serve to improve the function of the brace are thereby created. The brace may include means for securing the brace about a portion of the human anatomy and means for cushioning the portion of the human anatomy.

In accordance with a further aspect of the invention, the brace may also include a second sheet of compression molded resilient foam material stacked in a stack along with the first sheet of compression molded resilient foam material. The means for cushioning the portion of the human anatomy may include a compression molded bladder juxtaposed in between the first and second sheets of compression molded resilient foam material. The compression molded bladder may have first and second sheets of air-impermeable material with a foam pad in between. The air-impermeable sheets are sealed about the foam pad to seal the bladder. The bladder need not be filled with a foam pad, but may be filled with other materials such as a gel, a gas, a liquid, semi-flexible particles, and foam.

A brace may have a first layer of soft, less dense foam for placement toward the skin and a second layer of firm, dense foam for placement adjacent a brace wall. Additionally, the means for cushioning the portion of the human anatomy may be an interchangeable cushion pad. The sheet of resilient material may have a compression molded indentation for selectively receiving the cushion pad.

Other objects, features, and advantages of the invention will become apparent from a consideration of the following detailed description and the accompanying drawings.

BRIEF DESCRIPTION OF THE DRAWINGS

FIG. 7 is a cross-sectional view taken along line 7—7 of FIG. 6 showing the strut and the strut groove;

FIG. 8 is a close-up view of portion 8 of FIG. 4 showing a first outer layer of material, an inner layer of foam rubber, and a second outer layer of material;

FIG. 9 is a front view of an embodiment of a formed foam rubber knee brace having grooves for a bladder, a pump and a tube connecting the pump to the bladder.

FIG. 10 is a plot of displacement vs. load for compressed and uncompressed foam rubber;

FIG. 11 is a front view of a back brace according to the present invention;

FIG. 12 is a back view of the back brace of FIG. 11 according to the present invention;

FIG. 13 is a sectional view taken across line 13—13 of FIG. 11;

FIG. 14 is a front view of a first alternative embodiment of a related back brace;

FIG. 15 is a rear view of the back brace of FIG. 14;

FIG. 16 is a sectional view taken along line 16—16 of FIG. 14;

FIG. 20 is a sectional view of the second pad member taken along line 20—20 of FIG. 19;

FIG. 21 is a sectional view of the second pad member of FIG. 19 taken in Area 21 of FIG. 20;

FIG. 22 is a sectional view of a heel pad and strap taken along line 21—21 of FIG. 19;

FIG. 23 is a perspective view of a compression molded counter strap having compression molded grooves;

FIG. 24 is a sectional view of a compression molded counter strap taken along line 24—24 of FIG. 23.

DETAILED DESCRIPTION OF PREFERRED EMBODIMENTS

Before considering a particular preferred embodiment, it is useful to discuss the invention in general. A principal characteristic of the present support invention is regions of varying thickness and density. These regions are created by a process known as compression molding, wherein a combination of heat and pressure is applied to a sheet of material. The manufacturer varies the amount of heat and pressure that is applied in different areas of the material in order to reduce thickness in certain areas. The areas that are not compressed, or which are only slightly compressed, can constitute regions of extra padding. The material is typically a resilient open-cell material such as urethane, although the material might also be a foam closed-cell rubber such as neoprene.

The art of compression molding requires both special equipment and special skill. Therefore, a designer of a compression molded product will typically submit specifications to a commercial compression molding company, which will then manufacture the product. One such compression molding company is Rubatex Corporation of Bedford, Va.

FIG. 10 is a comparison of the stretch characteristics of compressed and uncompressed foam rubber. This figure was derived from tension tests of uncompressed, and compressed samples of neoprene that were supplied to the inventors by the Rubatex Corporation. Each of the samples had a testing length of 3 inches and a width of 1 inch. The uncompressed samples were 3/16 inch thick, and the compressed samples were 1/8 inch thick. As FIG. 10 illustrates, the compressed and uncompressed materials behave similarly at low loads. However, as the load increases, the compressed material tends to stretch more than the uncompressed material. By applying this principle to foam rubber orthopaedic support design, a designer may control the stretch characteristics of a support by varying the degree to which different regions of the support are compressed. Furthermore, because the support pressure of a foam rubber support is related to its stretch characteristics, the designer may simultaneously control the pressure that the brace exerts at different areas of an injured part of the human anatomy.

Figure 1:
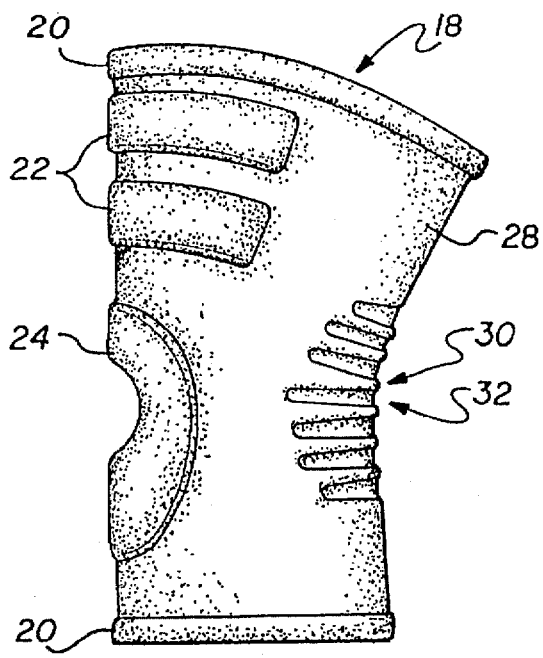
FIG. 1 is a side view of one embodiment of a formed foam rubber orthopaedic knee brace.

Now turning to one specific embodiment of the invention, FIG. 1 shows an orthopaedic knee brace 18. The brace has been compression molded to have a number of features. Strip pads 22 protect the flesh and muscle above the knee when the user either falls down or bumps into another object. Similar pads may be placed below the knee to protect the shin. Patellar buttress 24 supports and protects the patella. Main body 28 may be compression molded to have a generally uniform thickness and density, and therefore uniform stretch characteristics as may be desired for overall support.

Figure 2:
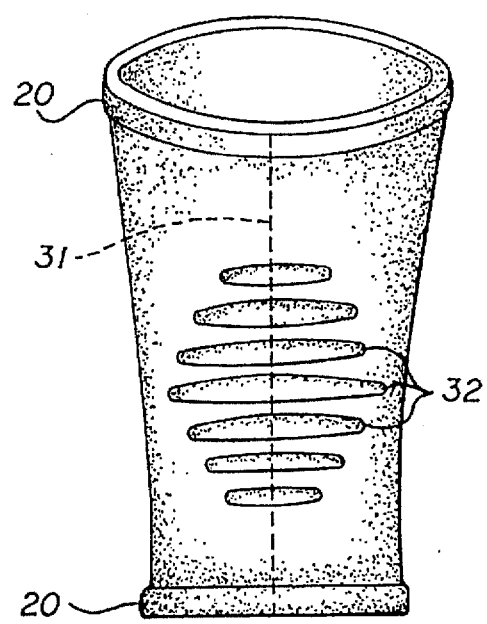
FIG. 2 is a rear perspective view of the formed foam rubber knee brace of FIG. 1.

The knee brace also includes compression molded transverse grooves 32 located in the rear popliteal area 30. These compression molded grooves 32 are shown in both FIGS. 1 and 2. Grooves 32 allow the rear popliteal area 30 to fold accordion style when the knee is bent. This feature overcomes the long standing problem of material bunching, which prevents the knee from flexing freely with traditional knee braces. Rear popliteal area 30 may have a generally relaxed thickness in order to help the knee bend. The sheet material is sewn together along sew line 31 as shown in FIG. 2.

Raised rims 20 act to anchor the knee brace onto the knee area. As discussed previously, and as shown in FIG. 10, compressed foam rubber stretches more easily than foam rubber that is not compressed or that is compressed relatively less. Consequently, rims 20 stretch relatively less than base 28, thereby causing rims 20 to behave like elastic bands mound the portions of the leg that are above and below the knee. Thus, the knee brace of FIG. 1 is self-anchoring without the use of straps.

Figure 3:
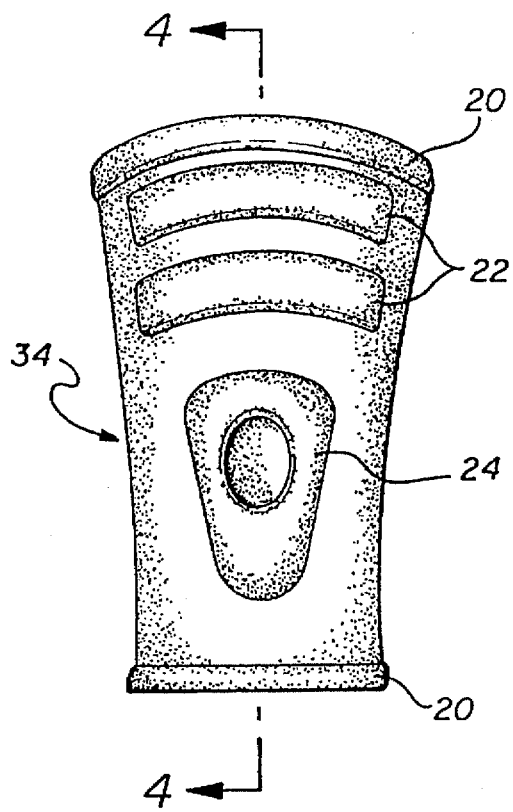
FIG. 3 is a front view of the formed foam rubber knee brace of FIG. 1.
Figure 4:
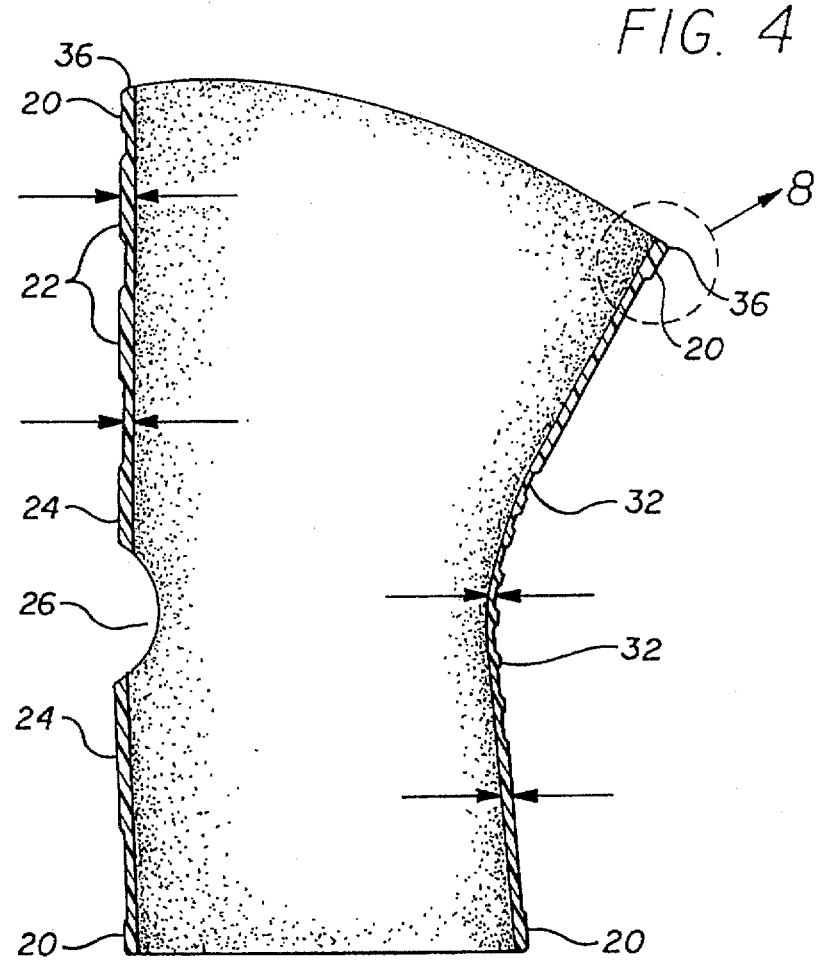
FIG. 4 is a sectional view of the formed foam rubber knee brace taken along the line 4—4 of FIG. 3.

The compression molded features of knee brace 18 are more particularly seen in FIG. 4, which is a cross sectional view of the brace taken at Section 4—4 of FIG. 3. FIG. 4 particularly shows such features as pads 22, patellar buttress 24, and transverse grooves 32. Also shown is patellar aperture 26, which allows the user to flex her or his knee with relative freedom. Note that the compression molding technique allows sudden discontinuities in height and density between raised and non-raised portions, thereby allowing the designer to create corresponding discontinuities in the pressure that the brace exerts on the limb.

FIG. 4 also illustrates molded edge 36, which rounds the interior of the edge away from the skin to reduce both allergy problems and irritation during exercise. FIG. 8, which is a close-up view of Section 8 of FIG. 4, shows a more detailed view of molded edge 36. FIG. 8 reveals that the knee brace 18 is formed from a material having three layers. The two outer layers 52 are typically a thin nylon or brushed nylon material. The middle layer 54 is typically a closed cell rubber such as neoprene. Molded edge 36 prevents the user's skin from coming into contact with middle layer 54, which is often allergenic. Furthermore, the skin does not come into contact with a rough edge, as it would if the edge was die cut.

Figure 5:
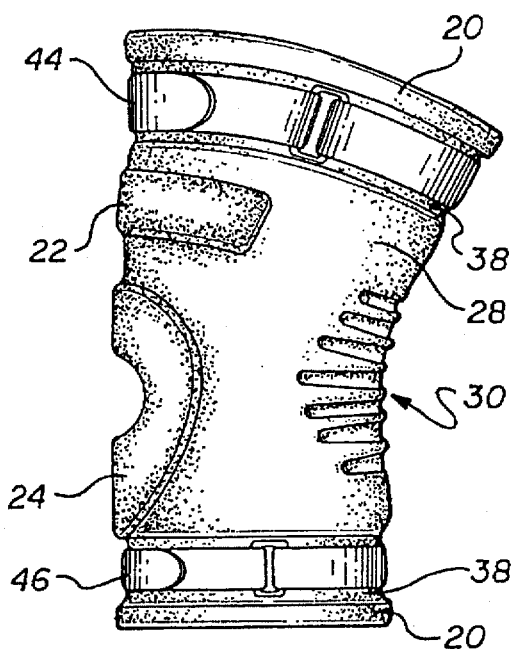
FIG. 5 is a side view of an embodiment of a formed foam rubber orthopaedic knee brace having grooves for straps.

FIG. 3 illustrates the overall appearance of the leg and knee brace 34. Several types of channels, grooves, and indentations can be compression molded into the brace. These channels and indentations serve to hold brace hardware into place, to prevent the hardware from protruding from the brace, and to serve as hardware locators during the manufacturing process. The strap grooves 38 are an example of this type of compression molded groove, as shown in FIG. 5. The strap grooves guide or maintain straps 44 and 46 in place so that there may be no need to sew the straps onto the brace itself. Note that the level of the straps is about even with base 28 of the brace, and the straps do not protrude. Thus, it is unlikely that the straps will catch on external objects when the brace is worn.

Figure 6:
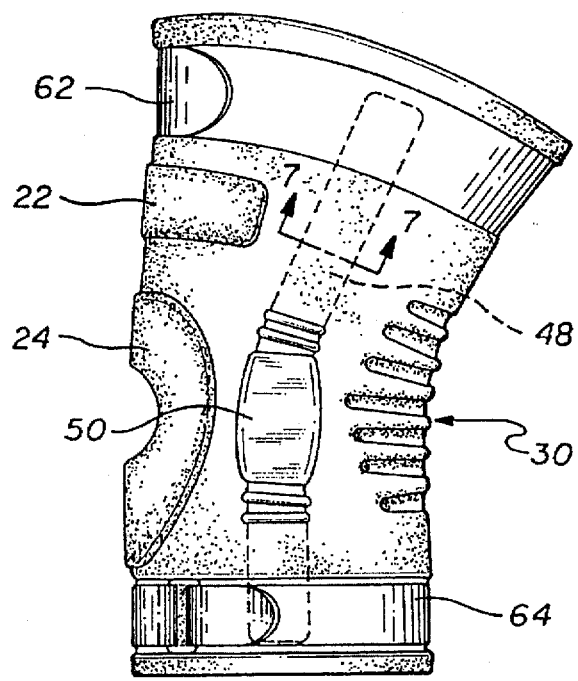
FIG. 6 is a side view of an embodiment of a formed foam rubber orthopaedic knee brace having grooves for struts and for straps.

FIG. 6 illustrates a knee brace having a compression molded channel for strut and hinge hardware, which serve to reduce the load that bears directly on the knee. The compression molded channel holds strut 48 and strut hinge 50 in place, and prevents strut 48 and strut hinge 50 from significantly protruding from the brace. FIG. 7, which is a cross sectional view taken along Section 7—7 of FIG. 6, shows strut 48 neatly resting inside strut channel 66. Strut 48 is covered by one of two outer layers 52, which are typically nylon or brushed nylon material. A second layer 68 of the same material lies underneath outer layer 52 and underneath strut 48. The base of the brace is an inner layer of material 54, which is typically foam rubber. Outer layer 52 lies flat over strut 48, such that the strut itself is not visible from the exterior of the brace. These strut channels 66 allow strut 48 to rest underneath straps 62 and 64, thereby allowing the user to secure the brace to her or his knee without interference from the strut mechanism.

FIG. 9 illustrates an air bladder, an associated air pump, and a tube to connect the air pump to the air bladder, all of which rest neatly inside compression molded indentations. The bladder 58 serves to support and protect the knee beyond what patellar buttress 24 can provide. Tube 60 connects pump 56 to bladder 58. The user may pump more or less air into the bladder to adjust the pressure that the bladder exerts upon the knee. Such air packs weigh very little, yet can add considerable support to the knee.

Similar channels and indentations can be compression molded into the brace for a variety of other types of hardware. For instance, indentations can be provided for gel packs, which are used either to protect against impact and/or for thermal therapy. A gel pack for protecting against impact may be permanently located underneath the surface of the knee brace, similar to the manner in which strut 48 is permanently buried underneath the surface of the knee brace in FIG. 7. Gel packs that are to be used for thermal therapy must be removable, and may rest inside a pouch partially defined by a compression molded indentation. In the case of heat therapy, the user first heats a gel pack, then inserts the gel pack into a gel pack pouch. Once the gel pack has cooled somewhat, the user replaces it with a freshly heated gel pack.

The following dimensions are provided by way of example and not of limitation. Referring to FIG. 1, the foam rubber sheet has an uncompressed thickness of 3/16". Pads 22, rims 20 and patellar buttress 24 are not compressed and have the same 3/16" thickness. Base 28 is compression molded to a thickness of 1/8". Transverse grooves 32 have a thickness of 1/16". Of course, numerous variations are possible. One such variation is to reduce the thickness of the entire popliteal area 30, thereby allowing the user to bend her or his knee more easily.

It should be noted that knee brace 18 is presented as just one of a multitude of possible embodiments of the invention. The invention encompasses a wide range of compression molded supports and braces for all other parts of the body. Thus, in addition to knee braces, the invention includes similar supports for elbows, thighs, wrists, ankles, backs, feet, and shins. A general method of compression molding supports may be defined as follows.

General Method of Compression Molding Supports

A method of manufacturing a compression molded support includes stacking at least one sheet or piece of support material, and optionally other sheets or pieces of support material, pads, bladders and/or support hardware, then compression molding the stack into a support. Generally speaking, the stack of material includes one or more inner layers of a sheet material, such as urethane foam or another resilient material, and outer layers of material such as LYCRA or brushed nylon, although these outer layers are not always necessary. A bonding step may include gluing adjacent layers or pieces of material together, or the layers may be separated by thin sheets of urethane or vinyl, which melt under the heat and pressure of the compression molding process and fuse or bond adjacent layers or pieces of material together.

The manufacturer may form a pre-inflated bladder within the support by including a sub-stack of material in the stack of support material. The substack is defined by an open-cell foam pad with a first sheet of urethane or closed-cell foam on one side of the open-cell foam pad and a second sheet of urethane or closed-cell foam on the other side of the open-cell foam pad. A rigid or semi-rigid sheet of material may optionally be stacked in between the open-cell foam pad and the second sheet of urethane or closed-cell foam to create a stay within the bladder. The stack of support materials are then compression molded in the area surrounding the open-cell foam pad, such that the first and second sheets of urethane or closed-cell foam are fused together about the open-cell foam pad, thereby creating a pre-inflated bladder within the support.

Alternatively, an inflatable bladder may be compression molded into the support. To do so, the first and second sheets of urethane or closed-cell foam may be stacked without a foam pad in between. A sheet of rigid material may be stacked in between the first and second sheets of urethane or closed-cell foam to create a stay, or the first and second sheets may be stacked directly against one another. An inflation tube is then inserted in between the sheets of urethane or closed-cell foam, with one end extending into the bladder interior and the opposite second end extending out of the stack of materials for connection with an external pump during inflation. Alternatively, the second end of the inflation tube may lead directly to a pump that is embedded in the stack of support materials. Once the inflation tube is in place, the stack of support materials is compression molded to fuse the first and second sheets of urethane together around a bladder perimeter.

Various channels, troughs, indentations and grooves can be molded into selected regions of the support for accommodating brace hardware and/or to alter the stretch characteristics in certain regions. Some of these have already been discussed in conjunction with the knee brace embodiments of the present invention. For instance, an indentation may be molded to accommodate a pump for inflating an internal bladder.

Compression Molded Back Braces

Another type of compression molded orthopedic support that falls within the scope of the present invention is a back brace that has portions that are compression molded. FIGS. 11–13 illustrate one embodiment of a compression molded back brace. The brace has an "interior" surface for placement adjacent to a user, and an "exterior" surface that faces the opposite direction, away from the user.

FIG. 11 illustrates the interior surface 101 of the brace. The brace is a belt member having a central portion 102 and a plurality of lateral support straps 104, 106, 105 and 110 connected to the central portion 102. Ventilation holes 112 extend through the central portion 102, which also includes a central cushion 114. The brace includes a fastening system or element adapted to attach the belt member in a desired position and with a desired fit around the user. A portion of this system is the hook material pad 116 which is sewn onto straps 110 and 108 with first stitching pattern 118.

FIG. 12 illustrates the exterior surface 120 of the brace of FIG. 11. Loop material pad 122 is sewn onto straps 110 and 108 with pattern of stitching 126, while loop material pad 124 is sewn onto straps 104 and 106 with pattern of stitching 118. Loop material pad 122 is part of the fastening system. The user wears the brace with the interior surface 101 of FIG. 11 against her body and central cushion 114 against her back. To fasten the brace in place, she pulls straps 104 and 106 across the front of her body so that loop material pad 122 is facing outwardly away from her body. She then pulls straps 110 and 108 across the front of her body and presses hook material pad 116 into contact with loop material pad 124, thereby fastening the brace in place. This hook and loop engagement system is commonly known as VELCRO.

FIG. 13 is a cross-sectional view taken along lines 13—13 of FIG. 11. As is readily seen, central portion 102 includes several layers of different material. Interior surface 101 is made of a hook-compatible material such as brushed nylon layer 130. A layer of resilient material 132 such as urethane foam is adjacent to the brushed nylon layer 130. A bladder 134 is adjacent to layer of resilient material 132. The bladder is defined by a first layer of urethane film or closed-cell foam 136, a second layer of urethane film or closed-cell foam 138, and a layer of resilient material such as urethane foam sandwiches in between the layers of urethane film. Another layer of resilient material 140 is adjacent to the bladder. Exterior surface 120 is defined by another layer of hook-compatible material 142 such as brushed nylon.

FIG. 13 shows that the ends of straps 108 and 106, respectively, are sandwiches in between layers of resilient material 130 and 142. The straps are held in place with layers of pressure sensitive adhesive at 144, 146, 148, and 150. A variety of commercial pressure sensitive adhesives may be used, including the 921 High Tech Adhesive manufactured by the 3M Company of St. Paul, Minn.

A key feature of the present invention is the use of compression molding to vary the thickness and density of the material in selected areas to improve the function of the brace. In the embodiment of FIGS. 11–13, the various layers of material are compression molded together in regions 152 and 154 of FIG. 13. The pressure and heat of the compression molding process fuse urethane or closed-cell foam layers 136 and 138 at bladder edges 156 and 158, thereby sealing bladder 134. The compression molding reduces the thickness and increases the density of the resilient material in regions 152 and 154. The compression molding also causes the pressure sensitive adhesive to bond straps 108 and 106 to layers of resilient material 132 and 140.

FIG. 14 shows one of many possible alternative embodiments of a compression molded back brace. As with the embodiment of FIG. 11, the embodiment of FIG. 14 is a belt member 200 having a central portion 202 and a plurality of lateral support straps 204, 206, 208 and 210 sewn on the central portion 202 by stitching patterns 254 and 256. Canvas covers 258 and 260 cover the support straps where they connect to central portion 202. The brace includes a fastening system or element adapted to attach the belt member in a desired position and with a desired fit around the user. A portion of this system is the hook material pad 216 which is sewn onto straps 210 and 208 with first stitching pattern 218.

Central portion 202 includes a central cushion 214. Central cushion 214 also includes a rigid stay 250, which FIG. 16 illustrates. The stay 250 may be made of a ³⁄₁₆" polyethylene sheet. The stay stiffens the central cushion in order to provide additional support to the back. Compression molded side bars 262 and 264 provide additional strength to the brace.

Central cushion 214 also includes compression molded buttons 252. These buttons are illustrated in FIGS. 14 and 15. The purpose of the buttons is to prevent the central cushion 214 from balling up or bulging against the user's back. Air is then free to move within the cushion to properly distribute the pressure against the user's back. The buttons also serve to limit the height of the bladder, particularly in embodiments employing an inflatable bladder.

FIG. 15 illustrates the exterior surface 220 of the brace of FIG. 14. Loop material pad 222 is sewn onto straps 210 and 208 with pattern of stitching 226, while loop material pad 224 is sewn onto straps 204 and 206 with pattern of stitching 218. Loop material pad 222 is part of the fastening system and interlocks with hook material pad 216 to fasten the brace onto the user.

The lateral support straps 204, 206, 208 and 210 are buttressed with a system of pull straps 270, as seen in FIG. 15. The pull strap system includes a first pair of pull straps 272, 274 and a second pair of pull straps 276, 278, both pairs secured with a lateral securement strap 280 to the middle of the back or outward surface of the central portion 202. A loop is provided at the bottom of the strap 282 so that a user can reach back and adjust the position of the brace.

The straps of the first pair 272, 274 overlap each other, converge towards one another and are sewn together and to the support straps 210 and 208 at outward location 284. The straps of the second pair 276, 278 are similarly oriented and are sewn together and to the support straps 204 and 206 at location 286. The pull straps are spaced a distance from the edges of the belt ends and towards the central portion 280. Then, when the belt ends are wrapped around the user and secured in place by the hook-and-loop fasteners 216, 226, the pull straps 272, 274, 276, and 278 pull against the central portion 280 and thereby pull the cushion 214 firmly against the sacro-lumbar region of the user's back, which is also known as the small of the back.

FIG. 16 illustrates a cross-section of the central portion 202 taken along line 15—15 of FIG. 14. The central portion is made by the method of manufacture described previously. Several layered pieces of material are compression molded together in certain areas to increase the material density and reduce the thickness of the resilient material in those areas. Central pad 214 of brace 200 includes an outward layer of brushed nylon 286, a first thin layer of urethane 288, a rigid sheet of polyethylene 250, a first sheet of urethane foam 290, a second thin layer of urethane 292, a second sheet of urethane foam 294, and an inward layer of LYCRA 296.

The first and second thin layers of urethane 288, 292, the rigid sheet of polyethylene 250, and the first layer of foam material 290 define a pre-inflated bladder. The bladder is formed by compression molding the brace about the perimeter of the foam material 290 at first and second thin layers of urethane 288, 292, which become fused together to seal foam material 290 and polyethylene 250 inside the bladder.

Central portion 202 further includes compression molded stays 262 and 264. The stays are formed in the brace by inserting strips of dense urethane foam 298, 299 in between the first layer of urethane 288 and the second layer of foam 294. Dense strips of urethane foam 298, 299 may be augmented by strips of rigid or semi-rigid material such as polyethylene in order to stiffen side bars 262 and 264.

Compression molded buttons 252 are also illustrated in FIG. 16. The buttons are highly compression molded to the point of being rigid. They may include air holes (not illustrated) punched in the center of the button in order to provide ventilation to the user.

With respect to a further embodiment of the present invention, it should be noted that the lateral support straps of the present invention need not be separate pieces attached to a central portion. Rather, the support straps and the central portion may be compression molded from one or more common sheets of resilient material. The support straps are therefore integral to the central portion of the brace.

Figure 17:
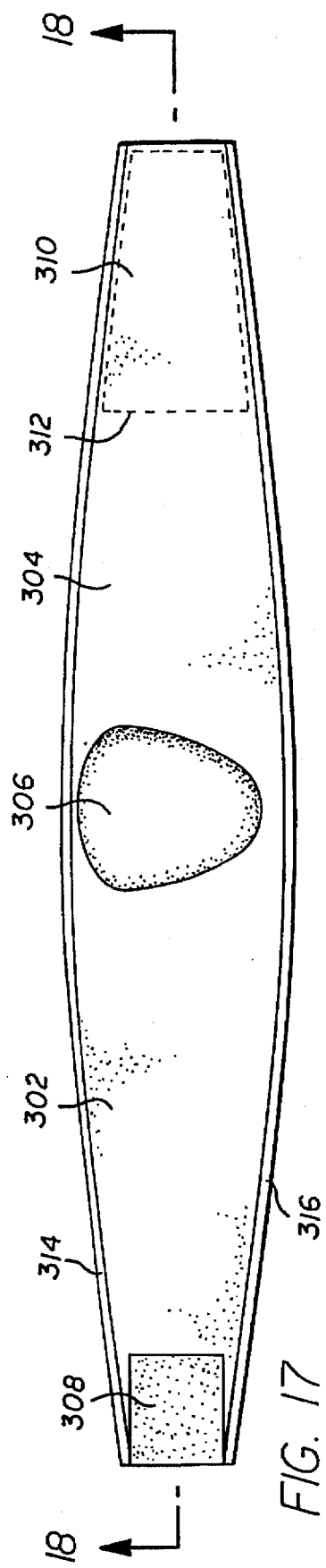
FIG. 17 is a front view of a second alternative embodiment of a back brace according to the present invention.
Figure 18:
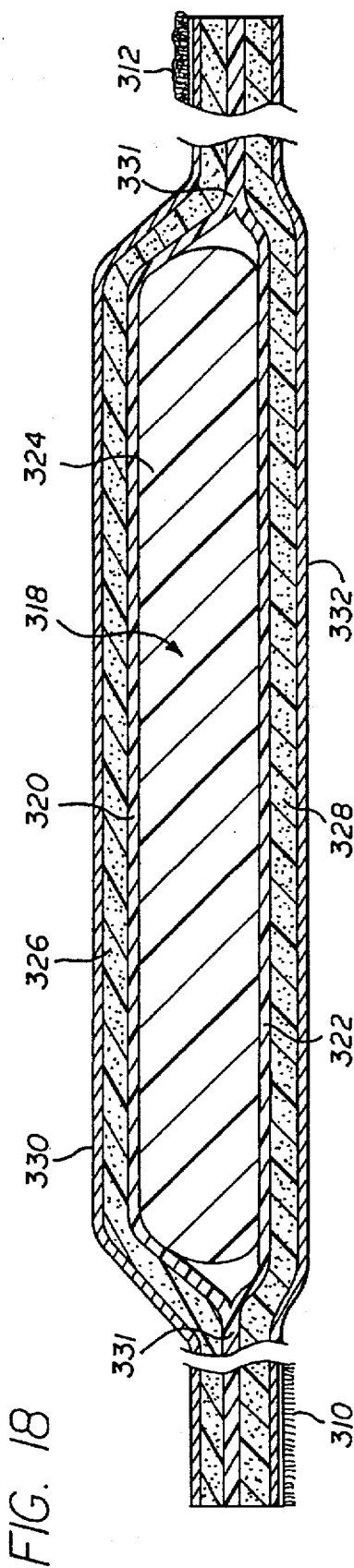
FIG. 18 is a sectional view taken along line 18—18 of FIG. 17.

FIGS. 17 and 18 illustrate such a brace, which has a central portion 300 and integral support straps 302 and 304. Central portion 300 includes a central cushion 306 having an interior bladder. A pad of hook-type material 308 is adhered to an outer end of support strap 302 on the inward side of the brace. A mating pad of loop-type material 310 is sewn with stitching pattern 312 to an outer end of support strap 304 on the outward side of the brace, as seen in FIG. 18. Border trim 314 and 316 cover the edges of the brace.

Central cushion 306 includes a bladder 318, which is defined by an inward urethane sheet 320, an outward urethane sheet 322, and a layer of urethane foam 324 encompassed by the inner and outer urethane sheets, as seen in FIG. 18. Sheet of urethane foam 326 is next to bladder 318 toward the inward side of the brace, and sheet of urethane for 328 is next to bladder 320 toward the outward side of the brace. The bladder is sealed by compression molding around the periphery of the bladder 331 to fuse layers 320, 322 together.

Layers of LYCRA material 330, 332 define the inward and outward surfaces of the brace. Material layers 330, 332 are glued to urethane foam layers 326, 328, respectively.

Ankle Braces Having Compression Molded Components

Figure 19:
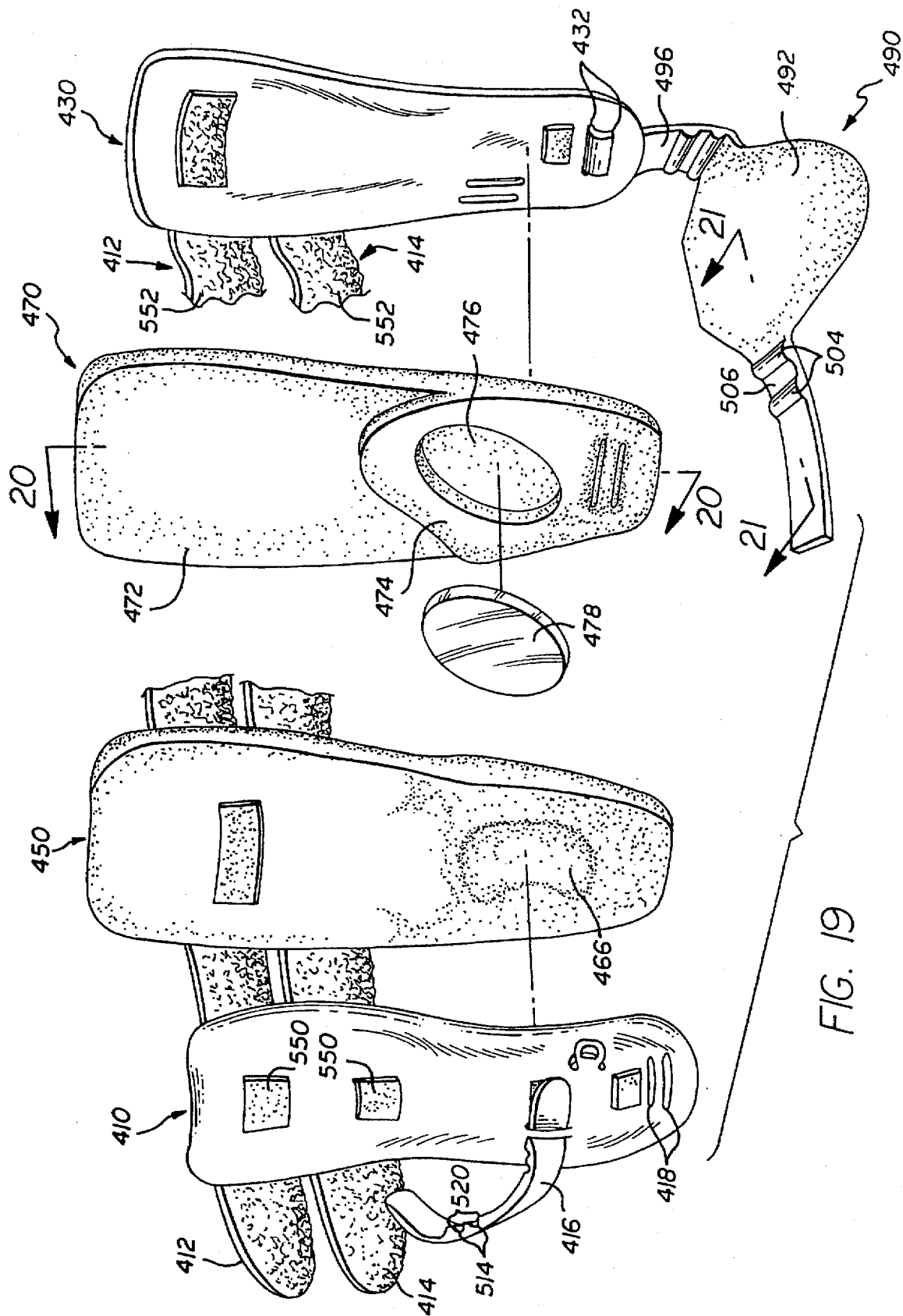
FIG. 19 is an exploded view of an ankle brace according to the present invention.

Another embodiment of the present invention is an ankle brace having compression molded components, such as that illustrated in FIGS. 19–24. As FIG. 19 shows, such a brace may include first and second side wall supports 410 and 430, first and second pad members 450 and 470, and a heel pad/heel strap member 490. First and second side wall supports 410 and 430 are generally made of a somewhat rigid plastic, such as polyethylene. Attachment straps 412, 414 and counter strap 416 hold the brace secure on the ankle. Attachment straps 412, 414 attach to the first and second side wall supports with a VELCRO-type fastening system utilizing hook-type material pads 550 and loop-type material 552 on one side of straps 412, 414 or vice-versa. A VELCRO-type system may also be used to attach first and second pads 450, 470 to side wall supports 410, 430.

As seen in FIG. 19, first and second pad members 450, 470 each include a compressed upper area such as 472, a less compressed, padded area such as 474, and a pad recess such as 476. An interchangeable pad 478 may be inserted into the pad recess 476. Interchangeable pad 478 may have a flat surface, or may have a concave shape to conform to the shape of the malleolus of the ankle. Interchangeable pad 478 may be a piece of compression molded resilient foam, or may be a gel or air pad, or any other type of pad.

FIG. 20 shows second compression molded pad member 470 in cross-section. Pad 470 includes an exterior layer of dense, firm foam 480 on the outer side wall support side of the pad, and another layer of softer, less dense foam 482 on the inner side of the pad. The arrangement of the soft foam/firm foam puts the lower density foam, which is softer, next to the skin where comfort is desired. The higher density foam, which is firmer, goes next to the shell to insure that the pad does not bottom out during use.

A "Pac-Man" pad 486 is included in the stack of material layers, on the exterior side of firmer foam layer 480. "Pac-Man" pad 486 is generally oval in shape but with a section removed to make space for the portion of counter strap 416 that protrudes on the interior side of second side wall support 430. The profile of "Pac-Man" pad 486 can be seen in FIG. 19, which shows identical "Pac-Man" pad 466. Outer layer of brushed nylon 484 covers the entire pad. FIG. 21 is a detailed sectional view showing the juxtaposition of the soft layer of foam 482, the firm layer of foam 480, and the "Pac-Man" pad 486.

Heel pad and strap member 490 includes heel pad 492 and heel straps 494 and 496. Heel pad 492 includes a layer of resilient foam 498, a layer of a non-stretch or limited stretch material 500, and another layer of resilient foam 502, as shown in FIG. 22. Layer of non-stretch material 500 may be a nylon mesh, a fabric, or any other material that does not stretch or that stretches only to a limited degree. Heel pad and strap assembly 490 are covered by upper and lower layers of LYCRA or brushed nylon 508, 510.

It should be noted that this concept of adding a layer of non-stretch or limited-stretch material may be extended to any of the compression molded components in any of the embodiments discussed in the present application where non-stretch or limited-stretch characteristics are desired.

Straps 494, 496 include compression molded layers of resilient foam 498, 502 which are compression molded to have click-stop ridges 504 and compression molded notch 506. With click-stop ridges 504 and notch 506, a user may pull a ridge through a heel strap slot 418 to secure the heel strap on side wall support 410. Such ridges and notches allow the user to adjust the length of the strap. Straps 494, 496 may have several notches and click-stop ridges, if desired. Compression molding allows the heel piece to be made to have sufficient cushioning under the heel, yet thin enough in the straps in order to fit through slots in the side wall supports.

FIG. 23 shows that counter strap 416 includes outer straps 510, 512, compression molded grooves 514, 516, click-stop ridges 518, 520, and compression molded achilles tendon portion 522, which provides means to properly orient and position the strap on the achilles tendon. FIG. 24 shows that counter strap 416 comprises an upper layer of LYCRA 526, a compression molded layer of resilient foam 528, and a lower layer of LYCRA 530.

A variation of the present ankle brace embodiment involves compression molding pads 450 and 470 to side supports 410 and 430, respectively. For instance, the manufacturer may place pad 450 next to side support 410, then compression mold both together to fuse pad 450 to side support 410. A thin layer of urethane, vinyl or the like may be interposed between pad 450 and support 410 prior to compression molding. The urethane will melt during compression molding, thereby bonding pad 450 to side support 410. The process of compression molding the pad to the substantially rigid side support eliminates the need to have a VELCRO type fastening system to hold the pad and the support together.

Figure 25:
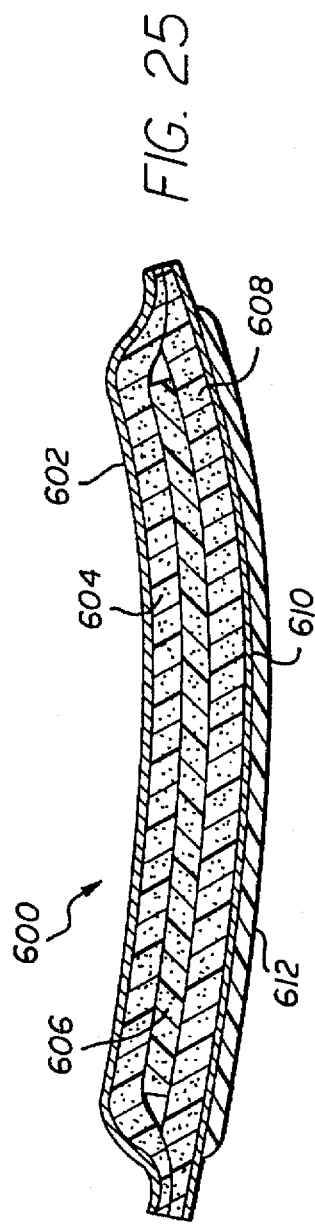
FIG. 25 is a sectional view of a form of compression-molded bladder.

It is considered important to further consider various alternative constructions of a compression-molded bladder. Referring to FIG. 25, an alternative compression-molded bladder construction may have walls of closed-cell foam or other gas-impermeable resilient material. FIG. 25 shows an orthopaedic support having a portion 600 with a compression-molded bladder. An important feature of this embodiment is that the bladder walls 604 and 608 are made of a resilient, air-impermeable material such as a closed-cell foam. Alternatively, solid rubber or other resilient, air-impermeable material may be used. The bladder walls are compression-molded around a bladder perimeter, also known as a bladder edge, to seal the bladder. Layers of brushed nylon or LYCRA material 602 and 610 (which may be air-permeable) are glued or otherwise bonded to the exterior of bladder walls 604 and 608. The resilient walled bladder of FIG. 25 may be also be used in place of the resilient liners 450 and 470 of the ankle brace of FIG. 19.

A bladder having resilient walls such as 604 and 608 has at least two advantages over bladders having film walls. First, resilient bladder walls reduce the number of layers of material that are needed to construct the support. The bladder wall can serve both to contain the gas within the bladder and as a source of padding. A second advantage is that the bladder walls will cushion the relevant portion of the anatomy even in the gas filling the bladder happens to escape. With a traditional bladder wall made of film, the walls of a deflated bladder would not provide any significant support to the user.

FIG. 25 illustrates an additional feature, namely, plastic shell 612 which underlies brushed nylon or LYCRA layer 610. Plastic shell 612 may be a side wall of an ankle brace (of the type shown in FIG. 19), a portion of a knee or elbow brace, a wall of a wrist brace, a stay for a back brace, or any other type of shell useful to the function of the particular brace. It should be further noted that the bladder may be pre-inflated by including a piece of open cell foam 606 in between bladder walls 604 and 608. Alternatively, the center of the bladder may be an empty space filled by means of an external pump, which is put into communication with the center of the bladder by way of an inflation tube or channel. As a further alternative, the bladder may be filled with gel, resilient beads, or other bladder filler. A rigid member may be included on the interior of the bladder for additional support.

A further embodiment of a bladder could have walls made of an open-cell foam with air-impermeable material bonded to at least one side of each wall. So, for instance, a bladder wall may be constructed of a piece or sheet of urethane foam with a thin piece of urethane material glued to the exterior side of the urethane foam in order to retain gas or other bladder filling medium within the bladder. A bladder may even have one wall made of a closed-cell foam and another wall made of another air-impermeable material, such as flexible plastic sheet material, so long as the two materials may be compression-molded together around the edge or periphery of the bladder.

In conclusion, it is to be understood that the foregoing detailed description and the accompanying drawings relate to preferred embodiments of the invention. Various changes and modifications may be made without departing from the spirit and scope of the invention. Thus, by way of example and not of limitation, the material used in the knee brace embodiments need not be nylon-covered neoprene, but could be another closed cell rubber, or an open cell foam such as urethane. The pads could be positioned in various places, such as below the knee to protect the tibial spine, tibial crest and tibial tubercle during a fall. The thickness of the base can be patterned to make the brace stretch more easily in certain directions than in other directions, and the stretch characteristics may be custom designed for particular injuries. The straps could be replaced with bands of a strong elastic material, which could be covered with nylon to make them invisible from the exterior.

The patellar buttresses could have a different shape or could be substantially larger than that shown in the drawings. Air pump 56 can be located in a variety of places. Similarly, the air pump can be an external unit that temporarily connects to the bladder to fill the bladder with air. Additionally, compression molded transverse grooves 32 may not exist in some embodiments where ease of bending is not desired. Instead, some knee braces may have a rigid member along rear popliteal side 30 to prevent any bending of the knee whatsoever.

Similar modifications may be made to the multitude of other embodiments of the present invention. With respect to the compression molded bladders, various stays or other support members may be positioned inside of the bladder before it is sealed in order to provide additional support. Various materials other than polyethylene, vinyl and closed-cell foam may be used to construct the outer walls of the bladder. The material must merely be impermeable to air and fuse during compression molding to seal the bladder. The bladder also need not be air-filled, but maybe filled with another gas, semi-rigid or flexible particles, one or more gel packs, liquids such as water, foam, or any other bladder filling known in the art. Additionally, it should be noted that more than one bladder may be compression molded into a support, if desired.

It should further be noted that the above-described back and ankle brace embodiments may incorporate various brace hardware, such as that described in conjunction with the knee brace embodiment and any other brace hardware appropriate to brace and ankle braces. The back and ankle brace embodiments may incorporate compression molded grooves such as those discussed with respect to the ankle brace. For instance, vertical grooves compression molded into the straps of the back brace can act as stays to better support the brace.

The central portion of a back brace embodiment may include a layer of non-stretch or limited-stretch material to control the stretch characteristics of the brace. Indeed, the layer of non-stretch or limited-stretch material may extend into the straps of an embodiment such as that depicted in FIG. 17, thereby limiting the stretch throughout the entire brace.

An entire line of orthopaedic supports falls within the scope of the present invention. In addition to the types of supports already discussed, the line may include wrist braces, neck braces, and a wide variety of compression-molded pads and inserts for other types of braces. These may include interchangeable receivable pads for insertion into compression-molded recesses in a support.

All of the compression-molded components of the present invention may be made from solid resilient material such as rubber. Compression molding would not significantly affect the density of such a solid material, but a desired effect could still be achieved by altering the thickness of the solid material in the compression-molded areas. As a consequence of the wide applicability of the present compression-molding technique to a variety of materials, the Load-Displacement characteristics illustrated in FIG. 10 will likely vary from material to material, with possible wide variations between certain materials.

The present invention is not limited to use on the human anatomy, but may be used on supports for various portions of the anatomy of animals. For instance, compression-molded supports may be fashioned for racehorses, dogs, cats and other animals. A particular advantage of the present invention is that the compression-molding process may be used to mold an unusual contour into a pad or support to properly fit an support an irregularly-shaped portion of the animal's anatomy.

The means for holding or securing the orthopaedic support onto a portion of the user's anatomy often includes straps, but the means may also relate to the resilient material itself which may form an elastic fit with the portion of the anatomy. Other means such as tape, adhesives, hook-and-loop material systems, laces, snaps, buttons, and any other systems known in the art.

The means for cushioning the portion of the body may include resilient material in sheet or piece form, various pads, bladders, gel packs, particle-filled pads, foams and/or compression-molded patterns, as well as other cushioning devices.

In sum, a wide variety of embodiments of body supports fall within the scope of the present invention. Accordingly, the present invention is not limited to the specific embodiments shown in the drawings and described in the detailed description.

We claim:

1. A compression molded orthopaedic device comprising:
   at least one sheet of resilient foam material having a predetermined thickness and density, said sheet of resilient foam material being compression molded by a heat and pressure process in certain areas to reduce the thickness and increase the density of said foam material in the compression molded areas, thereby creating a foam body having areas of less dense material which serve as padding and areas of more dense material which serve to facilitate the function of the orthopaedic device: and
   said compression molded areas retaining a compression molded thickness and density from the pressure and heat of the compression molding process alone.

2. A compression molded orthopaedic device as defined in claim 1, wherein the device is a compression molded brace for a portion of the human body and the device further comprises:
   means for securing the brace about a portion of the human anatomy; and
   means for cushioning the portion of the anatomy.

3. A compression molded orthopaedic device for as defined in claim 2, wherein:
   the device has a compression molded central portion; and
   said means for securing the brace about a portion of the human anatomy comprises lateral support straps attached to said central portion and a fastening element for fastening said lateral support straps together about the portion of the human anatomy.

4. A compression molded orthopaedic device as defined in claim 2, wherein:
   said sheet of resilient foam material is a first sheet of compression molded resilient foam material, said first sheet of compression molded resilient foam material being a firmer, denser foam material; and
   said means for cushioning the portion of the human anatomy comprises a second sheet of compression molded resilient foam material substantially juxtaposed to said first sheet of compression molded resilient foam material, said second sheet of compression molded resilient foam being softer, less dense foam material for placement substantially adjacent to a user's skin.

5. A compression molded orthopaedic device as defined in claim 2, wherein:
   said means for cushioning the portion of the human anatomy comprises an interchangeable cushion pad; and
   said sheet of resilient material has a compression molded indentation for selectively receiving said interchangeable cushion pad.

6. A compression molded orthopaedic device as defined in claim 2, wherein said sheet of resilient foam material is urethane foam.

7. A compression molded orthopaedic device as defined in claim 2, wherein the brace is an ankle brace and:
   said sheet of resilient foam material is a first sheet constituting a first compression molded pad for placement adjacent one side of an ankle;
   the brace has a second compression molded sheet of resilient foam material constituting a second compression molded pad for placement on an opposite side of the ankle from said first pad;
   the brace has two substantially rigid side walls which are placed outwardly of the ankle and said first and second pads; and
   said means for securing the brace about a portion of the human anatomy comprises straps which wrap around at least a part of the ankle and which connect to the substantially rigid side walls to secure the brace about the ankle.

8. A compression molded orthopaedic device as defined in claim 7, wherein:
   said first and second pads each include a compression molded detent; and
   said compression molded brace further includes interchangeable pads for selective insertion into said compression molded detents, thereby providing a variety of cushioning options to the user.

9. A compression molded orthopaedic device as defined in claim 7, wherein said first and second pads are provided with compression molded areas having a profile to match the malleolus of the ankle for a comfortable fit on the ankle.

10. A compression molded orthopaedic device as defined in claim 1, wherein:
    said sheet of resilient foam material is a first sheet of compression molded resilient foam material;
    said orthopaedic device further includes a second sheet of compression molded resilient foam material stacked in a stack along with said first sheet of compression molded resilient foam material.

11. A compression molded orthopaedic device as defined in claim 10 wherein the device further comprises a bladder between said first and second sheets of compression molded resilient foam material.

12. A compression molded orthopaedic device as defined in claim 11, wherein said bladder comprises first and second sheets of air-impermeable material and a foam pad between said first and second sheets of air-impermeable material, said first and second sheets of air-impermeable material being compression-molded about said foam pad to seal the bladder.

13. A compression molded orthopaedic device for a portion of the anatomy as defined in claim 11, wherein said bladder is filled with at least one material selected from the group consisting of a gel, a gas, a liquid, semi-flexible particles, and foam.

14. A compression molded orthopaedic device as defined in claim 11, wherein said bladder has bladder walls comprise sheets of air-impermeable material which are compression molded about a bladder perimeter to seal said bladder.

15. A compression molded orthopaedic device as defined in claim 14, wherein said bladder walls are a material selected from the group consisting of resilient closed-cell foam and solid rubber, whereby said bladder walls provide padding to the user even when the bladder is not inflated.

16. A compression molded orthopaedic device as defined in claim 1, wherein said orthopaedic device includes a compression-molded strap for an orthopaedic support.

17. A compression molded orthopaedic device as defined in claim 1, wherein said brace further comprises a sheet of substantially non-stretch material substantially in juxtaposition to said sheet of resilient foam material for limiting the stretch characteristics of the brace.

18. A compression molded orthopaedic device as defined in claim 17, wherein the device is a heel pad for an ankle brace.

19. An orthopaedic support comprising:

means for supporting a portion of the anatomy;

resilient foam material in sheet form comprising at least a part of said support, said foam material having a surface, a predetermined thickness and density in major areas of said support, and at least one compression molded area extending inwardly from said surface, the thickness of said foam material in one portion of said compression molded area being substantially less than said predetermined thickness and the density of said foam material at said portion of said compression molded area being greater than said predetermined density; and means for holding said orthopaedic support on a joint of the user's anatomy:

wherein said compression molded area has been subjected to a compression molded process comprising heat and pressure prior to any contact with the portion of the anatomy, said compression molded area retaining a compression molded shape from the pressure and heat of the compression molding process alone.

20. An orthopaedic support as defined in claim 19, wherein said support further comprises a bladder for providing additional padding to the portion of the anatomy, said bladder being substantially adjacent to said sheet of resilient foam material.

21. An orthopaedic support comprising:

a support body for supporting a portion of the anatomy, said support body constituting at least in part resilient material in sheet form;

said resilient material being compression molded prior to contact with the portion of the anatomy by heat and pressure in specific areas to vary the thickness and density of the material to improve the function of said support;

said support including areas subject to greater flexing in a first area and lesser flexing in other areas, said foam material being varied in thickness and density to give different resiliency in said first area than in said other areas; and said resilient sheet having a surface, a predetermined thickness in major areas of said support, and at least on compression molded area extending inwardly from said surface, the thickness of said support in one portion of said compression molded area being substantially less than said predetermined thickness.

22. An orthopaedic support as defined in claim 21, wherein said foam material in sheet form is a first sheet of compression molded, resilient foam material and said support further comprises a second sheet of compression molded, resilient foam material, said second sheet being substantially in juxtaposition to said first sheet.

23. An orthopaedic support as defined in claim 21, wherein said support further comprises a bladder to additionally pad the portion of the anatomy, said bladder being substantially adjacent to said sheet of resilient material.

24. A fail-safe orthopaedic support comprising:

a first sheet of resilient closed cell foam;

a second sheet of gas impermeable material, stacked together with said first sheet;

said first and second sheets being bonded together by a heat and pressure compression molding process to form a bladder having edges, said bladder being compression molded with heat and pressure about edges of the bladder to substantially seal the bladder; and means for securing said bladder to the anatomy of a user, whereby in the event the bladder becomes deflated, the resilient foam will still provide cushioning support.

25. An orthopaedic support as defined in claim 24 wherein said second sheet is formed of closed cell sheet material.

26. A fail-safe orthopaedic support as defined in claim 24 in which said bladder has a first mode in which it is inflated with a fluid to provide support to a portion of the anatomy.

27. A fail-safe orthopaedic support as defined in claim 26, wherein said bladder is inflated with air under pressure to provide support to the portion of the anatomy.

28. A compression molded orthopaedic back brace comprising:

a belt member having a central portion, a plurality of lateral support straps connected to said central portion, and a surface adapted to be placed against the back of a user;

at least one sheet of resilient foam material having a predetermined thickness and density, said sheet of resilient foam material being compression molded by a heat and pressure process in certain areas to reduce the thickness and increase the density of said foam material in the compression molded areas, thereby creating a foam body having areas of less dense material which serve as padding and areas of more dense material which serve to facilitate the function of the back brace;

said compression molded areas retaining a compression molded thickness and density from the pressure and heat of the compression molding process alone; and said belt member further comprising a fastening element that is adapted to secure said belt member in a desired position and with a desired fit around a user.

29. A compression molded orthopaedic back brace as defined in claim 28 wherein said central portion further comprises ventilation holes to provide ventilation to a user's back.

30. A compression molded orthopaedic back brace as defined in claim 28 wherein said lateral support straps are integral with said central portion.

31. A compression molded orthopaedic back brace as defined in claim 28 wherein said central portion further comprises a plurality of layers of material.

32. A compression molded orthopaedic back brace as defined in claim 31 wherein at least one of said layers of material has limited stretch characteristics, thereby limiting the stretchability of said central portion.

33. A compression molded orthopaedic back brace as defined in claim 28 wherein said central portion further comprises a bladder for providing additional cushioning to the user.

34. A compression molded orthopaedic back brace as defined in claim 28 wherein said central portion further includes a rigid support which limits the flexibility of at least part of said central portion.

35. A compression molded orthopaedic back support comprising:

a belt member;

at least one sheet of resilient foam material having a predetermined thickness and density, said sheet of resilient foam material being compression molded by a heat and pressure process in certain areas to reduce the thickness and increase the density of said foam material in the compression molded areas, thereby creating a foam body having areas of less dense material which serve as padding and areas of more dense material which serve to facilitate the function of the back brace;

said compression molded areas retaining a compression molded thickness and density from the pressure and heat of the compression molding process alone;

said central portion having an interior, said central portion comprising a compression molded bladder in said interior; and said central portion being secured to said belt member.

* * * * *